(12) United States Patent
Tischenko et al.

(10) Patent No.: US 8,090,089 B2
(45) Date of Patent: Jan. 3, 2012

(54) IMAGING METHOD AND DEVICE WITH DUAL READING SCANNER

(75) Inventors: Oleg Tischenko, München (DE); Christoph Hoeschen, Hebertshausen (DE); Yuan Xu, Eugene, OR (US)

(73) Assignees: State of Oregon Acting by and through the State Board of Higher Education on Behalf of the University of Oregon, Eugene, OR (US); Helmholtz Zentrum München Deutsches Forschungszentrum für Gesundheit und Umwelt (GmbH), Neuherberg (DE)

( * ) Notice: Subject to any disclaimer, the term of this patent is extended or adjusted under 35 U.S.C. 154(b) by 707 days.

(21) Appl. No.: 12/089,199

(22) PCT Filed: Oct. 25, 2006

(86) PCT No.: PCT/EP2006/010281
§ 371 (c)(1),
(2), (4) Date: Nov. 26, 2008

(87) PCT Pub. No.: WO2007/048590
PCT Pub. Date: May 3, 2007

(65) Prior Publication Data
US 2009/0245456 A1    Oct. 1, 2009

(30) Foreign Application Priority Data
Oct. 25, 2005    (EP) .................................. 05023312

(51) Int. Cl.
*G06T 11/00* (2006.01)
(52) U.S. Cl. .............. 379/149; 378/4; 378/16; 378/147; 382/131
(58) Field of Classification Search ................ 378/4–20, 378/145, 147, 149; 382/131
See application file for complete search history.

(56) References Cited

U.S. PATENT DOCUMENTS

| 4,647,779 A * | 3/1987 | Wong ........................ 250/363.03 |
| 6,946,658 B2 * | 9/2005 | Tai ............................ 250/363.03 |
| 2006/0050845 A1 * | 3/2006 | Juni ................................ 378/51 |

OTHER PUBLICATIONS

International Search Report dated Jan. 15, 2007, International Application No. PCT/EP2006/010281, International Filing Date Oct. 25, 2006.

(Continued)

*Primary Examiner* — Edward Glick
*Assistant Examiner* — John Corbett
(74) *Attorney, Agent, or Firm* — Klarquist Sparkman, LLP (57) ABSTRACT

An imaging method for imaging a region of investigation of an object comprises the steps of generating an energy input beam with an energy beam source, irradiating the region of investigation with energy input beam components of the energy input beam along a plurality of projection directions, the energy input beam components being formed with a frame mask being arranged between the energy input beam and the object and including frame mask windows, measuring first integrated attenuation values of the energy input beam components with an outer detector device arranged outside the frame mask, measuring second integrated attenuation values of the energy input beam components with a frame mask detector device being arranged on an inner surface of the frame mask, and reconstructing an image of the region of investigation based on the first and second integrated attenuation values. Furthermore, an imaging device for imaging a region of investigation of an object is described.

26 Claims, 7 Drawing Sheets

OTHER PUBLICATIONS

Bird et al., "X-ray all-sky monitoring and transient detection using a coded sphere telescope," Astron: & Astrophys. Supp. 17:131-136 (1996).

Willi A. Kalender, "Computed Tomography—Fundamentals, System Technology, Image Quality, Applications," Publicis MCD Verlag, Chapter 2, pp. 35-64 (2000).

Gabor T. Herman, "The Fundamentals of Computerized Tomography: Image Reconstruction from Projections," Academic Press, Chapter 6, pp. 90-107 (1980).

R. Marr, "On the Reconstruction of a Function on a Circular Domain from a Sampling of its Line Integrals," J. Math. Anal. Appl. 45:357-374 (1974).

F. Natterer, "The Mathematics of Computerized Tomography," SIAM, pp. 1-212 (2001).

F. Natterer and F. Wuebbeling, "Mathematical Methods in Image Reconstruction," SIAM, pp. 1-187 (2001).

C. Dunkl and Yuan Xu, "Orthogonal Polynomials of Several Variables," Cambridge University Press, Chapter 6, pp. 225-254 (2001).

Yuan Xu, "Funk-Hecke Formula for Orthogonal Polynomials on Spheres and on Balls," Bull. London Math. Soc. 32:447-457 (2000).

Yuan Xu, "Representation of Reproducing Kernels and the Lebesgue Constants on the Ball," J. Approximation Theory 112:295-310 (2001).

* cited by examiner

IMAGING METHOD AND DEVICE WITH DUAL READING SCANNER

ACKNOWLEDGEMENT OF GOVERNMENT SUPPORT

This invention was made with government support under Grant No. DMS-0201669awarded by the National Science Foundation. The government of the United States of America has certain rights in the invention.

CROSS REFERENCE TO RELATED APPLICATIONS

This is the U.S. National Stage of International Application No. PCT/EP2006/010281, filed Oct. 25, 2006, which was published in English under PCT Article 21(2), which in turn claims the benefit of European Application No. 05023312.1, filed Oct. 25, 2005. Both applications are incorporated herein by reference.

TECHNICAL FIELD

The present invention relates to a method for imaging a region of investigation of an object on the basis of Radon data comprising a plurality of projection functions measured corresponding to a plurality of predetermined projection directions relative to the object. In particular, the present invention relates to a computer tomography (CT) imaging method. Furthermore, the present invention relates to a device for imaging a region of investigation, e.g. a CT device, in particular on the basis of the above imaging method.

TECHNICAL BACKGROUND

The non-destructive investigation of samples is an important objective in various technical fields like material sciences, non-destructive testing, medical examinations, archaeology, construction technique, techniques concerning security matters etc. One approach for obtaining an image of a sample e.g. by computer tomography is based on an irradiation through a sample plane from different projection directions with X-rays, followed by the reconstruction of the sample plane on the basis of attenuation data measured at different directions. The entirety of the measured attenuation data can be described in terms of so-called Radon data in a Radon space.

Different reconstruction methods for Radon data are known today. For an introduction to the mathematical and physical principles of conventional image reconstruction, reference is made to the textbooks "Computed Tomography—Fundamentals, System Technology, Image Quality, Applications" by W. A. Kalender (1$^{st}$. edition, ISBN 3-89578-081-2); "Image Reconstruction from Projections: The Fundamentals of Computerized Tomography" by G. T. Herman, Academic Press, 1980; and "Einführung in die Computertomographie" by Thorsten M. Buzug (Springer-Verlag, Berlin 2004). The conventional reconstruction methods can be summarized as iterative reconstruction methods and filtered back-projection methods.

The iterative reconstruction is an approximation method based on a plurality of iteration steps. The essential disadvantage of the iterative reconstruction of higher resolution images is that the iteration leads to extremely long calculation times. The filtered back-projection method relies in principle on the Fourier-slice theorem describing a relationship between the Fourier transform of the Radon data and Fourier transformed image data. A general disadvantage of using the Fourier-slice theorem lies in the fact that an interpolation step in the reconstruction results in errors and artifacts which have a tendency to increase with increasing space frequency. This disadvantage can only be avoided by using detectors with high resolution. However, the application of these detectors is limited in terms of dose burden, costs and data processing time.

An improved method of reconstructing image functions from Radon data is described in EP 04031043.5 (unpublished on the filing date of the present patent specification). With this method of using orthogonal polynomial expansions on the disk (in the following: OPED algorithm), an image function representing the region of investigation is determined from Radon data as a sum of polynomials multiplied with values of projection functions measured corresponding to a plurality of predetermined projection directions through the region of investigation. The OPED algorithm has essential advantages in particular in terms of computational time reduction, noise reduction and improved imaging resolution.

Figure 13:
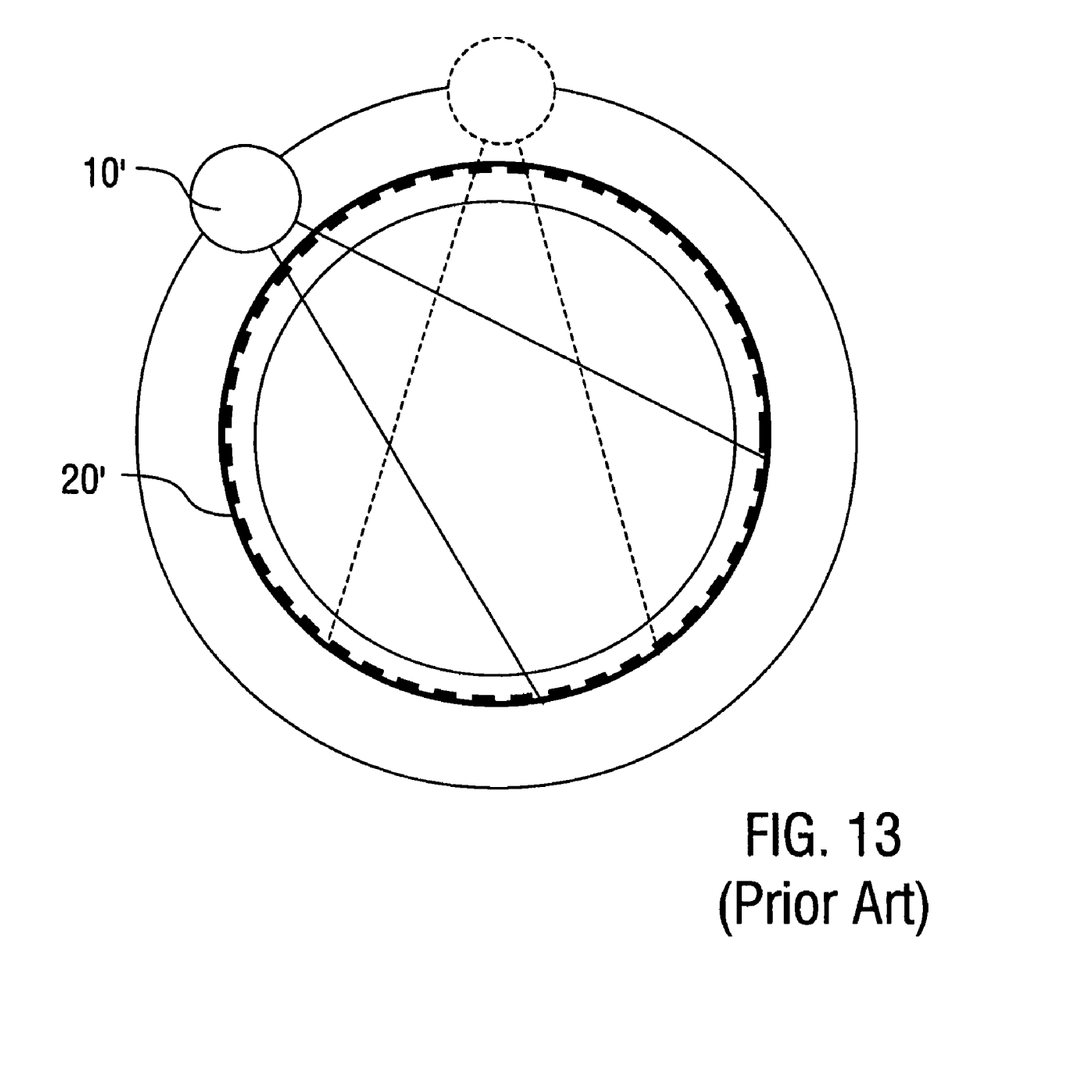
FIG. 13 a schematic illustration of a conventional imaging device (prior art).

Conventional computer tomography devices used for collecting Radon data comprise an X-ray source for irradiating the object, a detector device for measuring attenuated irradiation passing through the object and a holding device for holding the object. The holding device is arranged in a gantry, which comprises a carrier for a rotatable irradiation unit with the X-ray source and the detector device. With the so-called 4th generation of computer tomography devices, the rotatable source-detector-unit is replaced by a combination of a rotatable X-ray source 10' with a fixed detector ring 20' as illustrated in FIG. 13 (see the above text book "Einführung in die Computertomographie" by Thorsten M. Buzug, page 51). The detector ring 20' includes about 5.000 detector elements arranged on a circle around the object. In order to avoid an irradiation through detectors near the X-ray source, the conventional technique includes a dynamic inclination of the detector ring 20'. The dynamic inclination represents a disadvantage as it requires a complex structure and inclination control of the detector ring.

The conventional computer tomography devices have a further disadvantage in that not all irradiation applied to the object is collected and transferred to useful reconstruction data. Therefore, the object, e.g. a patient is subjected to an unnecessary high irradiation dose.

The above disadvantages are associated not only with the conventional CT imaging, but also with all available reconstruction methods related to Radon data.

OBJECTIVE OF THE INVENTION

The objective of the invention is to provide an improved imaging method for imaging a region of investigation of an object by reconstructing an image function from collected Radon data, leading to an increased range of applications in non-destructive investigations and avoiding the disadvantages of the conventional imaging techniques. In particular, the objective of the invention is to provide an imaging method, wherein all irradiation applied to the object is collected and used to provide Radon data for reconstructing the image function, so that the irradiation dose during imaging can be reduced. Furthermore, the imaging method should be capable of reconstructing image functions with increased resolution without the drawback of high computational time. Another objective of the invention is to provide an improved imaging device for imaging a region of investigation by reconstructing collected Radon data. According to a particular aspect, the objective of the invention is to provide the imaging device which allows a reduction of an amount of energy input (e.g. radiation dose) and scattering effects within the region of investigation.

SUMMARY OF THE INVENTION

Relating to the imaging method, the present invention is based on the general technique of collecting Radon data by measuring two groups of integrated attenuation values of energy input beam components, which are formed with a frame mask surrounding a region of investigation. The first group of integrated attenuation values are measured with an outer detector device being arranged outside the frame mask, while the second group of integrated attenuation values are measured with a frame mask detector device being arranged on an inner surface of the frame mask.

An energy input beam is generated with an energy beam source device arranged on an outer side of the frame mask. The energy input beam components are shaped with frame mask windows of the frame mask. Each energy input beam component is measured with one of the outer detector device or frame mask detector device. The group of first integrated attenuation values is measured with energy input beam components, which pass through pairs of frame mask windows arranged on opposite sides of the region of investigation. The group of second integrated attenuation values is measured with energy input beam components, which pass through frame mask windows and hit the frame mask detector on the inner surface of the frame mask.

Accordingly, the Radon data collection of the invention is improved such that every energy beam, e.g. X-ray beam that enters a region of investigation in the object is captured by the detectors and counted for. On the other hand, all measured attenuation values can be used for reconstructing an image function, so that every energy beam photon is used in the reconstruction and the energy beam dose, e.g. X-ray dose can be reduced without a reduction of the signal to noise ratio.

In particular, the imaging method of the invention comprises the steps of positioning the object within the frame mask, generating the energy input beam with the energy beam source being arranged outside the frame mask, irradiating the region of investigation with the energy input beam components along a plurality of projection directions, measuring the first and second groups of integrated attenuation values of the energy input beam components, and reconstructing the image of the region of investigation based on the first and second integrated attenuation values. The irradiating step comprises a setting of the projection directions, which are defined by the frame mask.

Contrary to the conventional tomography devices of the 4th generation, any movement of the frame mask like e.g. the conventional dynamic inclination can be omitted as the region of investigation is irradiated through the frame mask windows. The frame mask windows fulfill three functions. Firstly, the energy beam is transmitted through the mask to the region of investigation and the outer detector device. Furthermore, the energy beam components are shaped by the mask. Finally, sets of parallel energy beam components are formed by the mask as outlined below.

The term "region of investigation" (ROI) used herein generally refers to an object to be imaged or a part thereof. Generally, the ROI can be described as a 2-dimensional entity. For reconstructing a 3-dimensional image of the object, a plurality of ROI's is imaged.

The term "projection direction" used herein generally refers to the linear course of an energy input beam through the ROI in 3-dimensional space. The projection direction can be defined by angles relative to a coordinate system used.

The Radon data measured at the ROI comprise a set of projection functions, which have been determined corresponding to a plurality of predetermined projection directions running through the ROI. Each projection function comprises data, which are collected with a certain number, which might in theory be infinite large, of "projections" parallel to the current projection direction. These projections are characterized by integrating over one-dimensional lines. By measuring a sufficient number of these integrated "projections", an image function of the object can be reconstructed from the Radon data.

The values of the projection functions generally are determined by the modification (in particular attenuation, e.g. by absorption or scattering) of an energy input beam travelling through the ROI along the respective projection direction.

According to a preferred embodiment of the invention, the image function of the ROI is reconstructed as a superposition of a first sum of polynomials multiplied with values of first projection functions obtained from the first group of integrated attenuation values and a second sum of polynomials multiplied with values of second projection functions obtained from the second group of integrated attenuation values. Preferably, a linear superposition is provided. Firstly, the reconstruction algorithm described in EP 04031043.5 (OPED algorithm) is applied to the groups of attenuation values measured with the frame mask and outer detectors, respectively. Subsequently, the images obtained with the different groups of attenuation values are superimposed. Accordingly, the advantages of the OPED algorithm, which are described in EP 04031043.5, can be completely obtained with the imaging method of the invention.

Preferably, the projection functions subjected to the OPED algorithm are obtained from the first and second groups of integrated attenuation values measured with detectors sensing the corresponding first and second groups of parallel energy input beam components. Due to the scanning geometry provided by the frame mask, the groups of parallel energy input beam components are created automatically. The fixed geometry of the frame mask ensures that each detected beam component belongs to a plurality of parallel energy input beam components.

A further important advantage of the invention is given by the fact that the application of the imaging method is not necessarily restricted to the implementation of the above OPED algorithm but even possible with other algorithms for reconstructing the image. According to a further embodiment of the invention, the image reconstructing step comprises the implementation of a filtered back-projection algorithm (FBP algorithm). This embodiment of the invention has particular advantages in terms of availability of FBP software tools and compatibility with conventional data processing techniques, but it is not so suitable as using the OPED algorithm.

The imaging method of the invention comprises in particular the step of irradiating the ROI with the energy input beam components shaped by the frame mask along a plurality of different projection directions distributed over an angle range of at least 180°. The frame mask and the object generally are fixed relative to each other at least in a plane including the projections directions. The projection directions can be set by various techniques.

According to a preferred embodiment of the invention, the projection directions are set by moving the energy beam source and the frame mask relative to each other. Preferably, the energy beam source device comprises one single energy beam source only, which is movable around the frame mask.

Alternatively, the moving energy beam source can comprise more then one single energy beam source, e.g. two, three or more energy beam sources. With this embodiment, the projection directions are set by moving the energy beam source (s) relative to the fixed frame mask with the object and by collecting the data according to particular angle positions relative to the ROI. This embodiment with a single movable energy beam source has the advantage of avoiding any shortage of space for arranging the outer detector device in an opposite position relative to the energy beam source. Preferably, the energy beam source(s) is(are) continuously moved.

According to a further preferred embodiment of the invention, the outer detector device comprises one single outer detector array being movable around the frame mask for measuring the first integrated attenuation values with varying projection directions. If the moving energy beam source comprises more then one single energy beam source, the outer detector device correspondingly comprises a plurality of single outer detector arrays. The outer detector array(s) is(are) movable synchronously with the energy beam source device, so that the projection directions can be set automatically by moving the combination of energy beam source device and outer detector device to a particular angle position relative to the ROI.

According to a particularly preferred embodiment of the invention, the energy beam source and the outer detector array are simultaneously rotated around the frame mask for setting the projection directions. Preferably, both components are arranged on a common carrier surrounding the frame mask and the ROI. The particular advantage of this embodiment is given by the fact that the synchronous rotation of the energy beam source device and the outer detector device around the ROI can be provided with a conventional imaging device, like e.g. a computer tomography device.

According to a further alternative, the energy beam source and the outer detector device are fixed, while the projection directions are set by moving, e.g. rotating the frame mask and the object between the source and detector devices. This embodiment has particular advantages for micro CT applications, e.g. with small objects.

According to a yet another alternative, all components are fixed. In this case, the energy beam source device comprises a plurality of single sources distributed around a circumference of the frame mask adjacent to corresponding outer detector arrays. The projection directions are set by activation of the single sources with subsequently varying irradiation angles relative to the object.

The imaging method of the invention can be applied with different types of energy input beams used for providing the Radon data. The term "energy input beam" used herein refers to all types of a physical quantity, which travels along a straight line (or an essentially straight line) through the ROI while the energy carried is changed due to an interaction with the ROI. In particular, the term "energy input beam" covers electromagnetic radiation or particle radiation. Preferably, the energy input beam comprises X-rays. If an X-ray source device is used as the energy beam source device, conventional computer tomography devices upgraded with the frame mask can be used for implementing the imaging method of the invention.

Relating to the device, the present invention is generally based on providing an imaging device having an energy beam source device arranged on a carrier surrounding an object under investigation and a detector device for measuring radiation from the energy beam source transmitted through the object. The imaging device is provided with a frame mask surrounding the object in at least one plane according to the orientation of ROI and including frame mask windows that shapes energy beam components. Furthermore, the frame mask windows define a plurality of available projection directions for irradiating the ROI. The detector device comprises an outer detector device and a frame mask detector device. The outer detector device is arranged outside the frame mask, while the frame mask detector device comprises frame mask detectors arranged between the frame mask windows on an inner surface of the frame mask. With the frame mask, a new detection geometry is provided, that uses equally spaced projection angles relative to the ROI and that transforms energy beams from the energy beam source device having e.g. a fan beam geometry to parallel energy beam components automatically.

Preferably, the frame mask has a shape of a ring or flat cylinder with an axial extension covering the ROI. Alternatively, the frame mask has a shape of a tube or long cylinder with an axial extension covering the whole object. Particularly preferred is a ring or tube shaped frame mask with a circular cross-section. With the circular cross section, advantages for an effective implementation of the image reconstruction algorithms are obtained.

Advantageously, the frame mask and the holding device have a fixed position relative to the carrier. In this case, at least one of the source and detector devices can be moved, e.g. rotated around the frame mask for data collection. Alternatively, all components can be fixed in space, if the source and detector devices comprise a plurality of single sources and detector arrays distributed around the holding device.

According to a preferred embodiment of the invention, the energy beam source device comprises a single energy beam source being movable arranged on the carrier. Advantageously, one single energy beam source is sufficient for setting varying projection directions. Further advantages are obtained if both the single energy beam source and a single outer detector array form a common unit arranged on the carrier, which is included in a CT gantry as it is known from conventional CT devices.

According to a further preferred embodiment of the invention, the frame mask windows have equal sizes, so that a uniform irradiation of the ROI and equal dimensions of the energy beam components projected on a plane outer detector are obtained. Preferably, the outer surface of the frame mask is provided with a shielding, which has advantages for a protection of frame mask detectors against irradiation.

According to an advantageous embodiment of the invention, the imaging device is provided with a reconstruction circuit being adapted for an image reconstruction based on attenuation values detected with the detector device.

Preferred applications of the inventions are in the technical fields like material sciences, non-destructive imaging, non-destructive testing, medical examinations, archaeology, construction technique, and techniques concerning security matters.

BRIEF DESCRIPTION OF THE DRAWINGS

Further details and advantages of the invention are described in the following with reference to the attached drawings, which show in.

EMBODIMENTS OF THE INVENTION

The invention is described in the following with reference to the preferred application in computer tomography. It is emphasized that the invention can be implemented in an analogous way with the application of other types of energy input beams (like e.g. neutrons or light, e.g. in the VIS or IR range). Furthermore, the following description of the preferred embodiments mainly refers to the scanning geometry, data collection and data processing. The scanning geometry is described with reference to a fixed frame mask and a rotating source-detector unit. The invention can be implemented with a fixed source-detector unit and a rotating frame mask and object in an analogue way. Details of the CT devices used for implementing the invention are not described as long as they are known from conventional CT devices.

1. Imaging Device of the Invention

Figure 1:
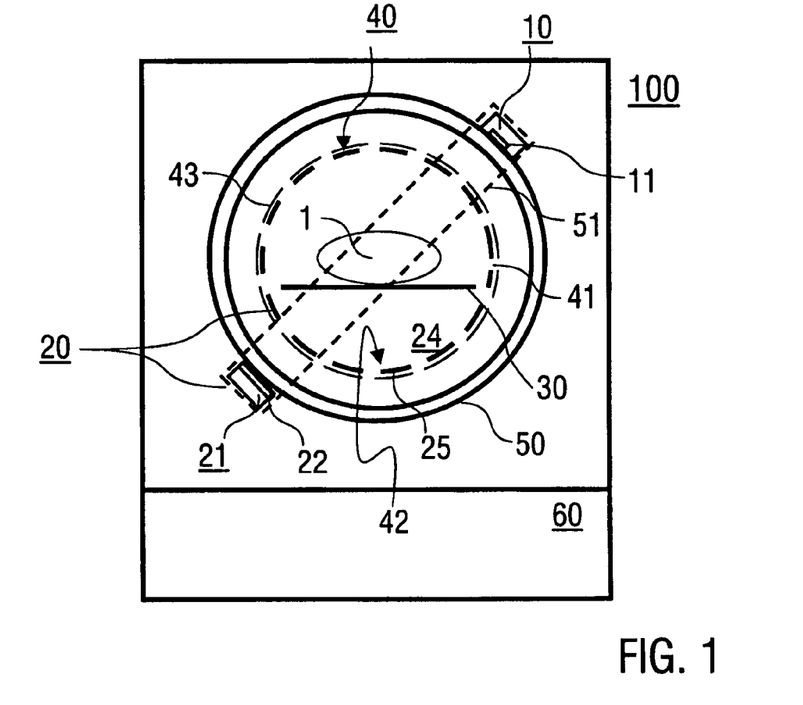
FIG. 1 a schematic representation of an embodiment of an imaging device according to the invention.

FIG. 1 schematically illustrates an embodiment of the imaging device 100 according to the invention, which comprises the energy beam source device 10 arranged on a carrier 50, the detector device 20 which comprises an outer detector device 21 arranged on the carrier 50 and a frame mask detector device 24 arranged on an inner surface of the frame mask 40, a holding device 30 for accommodating an object 1 and a reconstruction circuit 60.

The components 10, 30 and 50 are structured, as it is known from CT devices, e.g. current medical CT-systems. In particular, the energy beam source device 10 comprises a movable X-ray source 11 combined with the outer detector device 21 as a source-detector-unit 51. The source-detector-unit 51 is arranged on the carrier 50, which is e.g. a guide rail as it is known from a conventional CT gantry. The carrier 50 is illustrated as a circle allowing the rotation of the energy beam source device 10 and the outer detector device 21 around an object 1. According to a modification, the source carrier can have an elliptic shape or another shape. This can represent an advantage in terms of an adaptation to the geometry of the object to be investigated. The holding device 30 is e.g. a carrier table as it is known from CT systems or any other carrier or substrate holder for arranging and adjusting the object 1 relative to the energy beam source device 10 and the detector device 20. Further components like a control device, a display device etc. (not shown) are provided for as they are known per se from prior art devices.

The outer detector device 21 comprises a detector array 22, which is movably arranged on the carrier 50 opposite to the energy beam source device 10. With this structure, the projection direction through the ROI (parallel to the plane of drawing) can be set by rotating the source-detector-unit 51 with components 10, 21 around the holding device 30. The detector array 22 is a linear or 2-dimensional array of sensor elements being arranged on a curved, e.g. cylindrical or spherical (see FIG. 2) or a planar (see FIG. 5) reference surface.

The frame mask 40 (schematically shown) comprises a ring-shaped component with an outer side, where the energy beam source device 10 and the outer detector array 22 are arranged. The frame mask 40 includes frame mask windows 41 being spaced from each other with a predetermined arc length. The frame detector device 24 comprises a plurality of single frame detectors 25, which are positioned on an inner surface 42 of the frame mask 40 between the frame mask windows 41. Each frame detector 25 comprises a single sensor. An X-ray shielding material 43, like lead or tungsten is used for making the frame mask 40 or at least for covering the outer surface of the frame mask 50 according to the positions of the frame mask detectors 25.

The frame mask 40 is fixed relative to the carrier 50. For recording 2-dimensional images, the frame mask 40 is fixed relative to the holding device 30 as well. A structure (not shown) holding the frame mask 40 in position and carrying electrical connections of the frame mask detectors 25 is provided. The frame mask 40 has a ring or cylindrical shape with a cross-section (usually circular cross-section) aligned with a reference plane, in which the rays from the X-ray source 11 to the outer detector device 21 are travelling. The object 1 is arranged such that the ROI is aligned in this reference plane. The corresponding technique for the case of reconstructing 3-dimensional images is described below.

The reconstruction circuit 60 includes a computing unit as it is known from conventional CT devices. According to the invention, the computing unit includes circuits adapted for implementing the steps of constructing the projection functions and reconstructing the image of ROI (see below).

The frame mask 40 and the source-detector-unit 51 represent main parts of the imaging device, which determine both the irradiation and the measurement according to the invention. These parts are further characterized with reference to FIG. 2.

Figure 2:
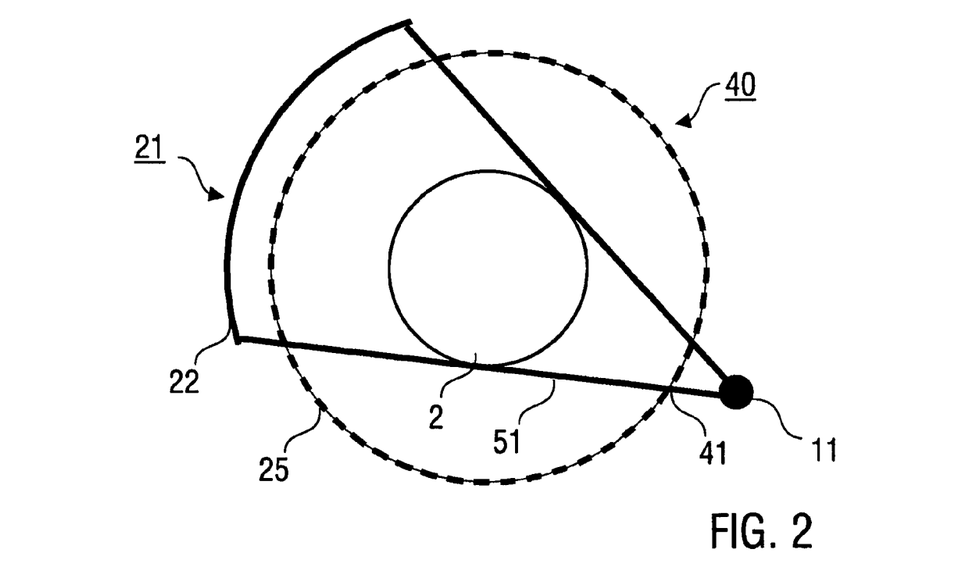
FIG. 2 a further illustration of the geometry of an imaging device according to the invention.

The frame mask 40 with the frame mask detectors 25 is arranged at the boundary of a disk, that contains the ROI 2. In the context of the algorithms described below, this disk is considered as the unit disk. Both the frame mask 40 and the disk are fixed. The frame mask detectors 25 represent channels of the frame mask detector device 24. Each of the frame mask detectors 25 comprises a single sensor with a 1-dimensional or 2-dimensional design. There are 2m+1 frame (m natural number) mask detectors 25 distributed along the inner surface of the frame mask 40. Each frame mask detector 25 has the same radial width equal to the arc length $\pi/(2m+1)$ on the unit circle. The centres of the frame mask detectors 25 are located at $2j\pi/(2m+1)$ (with $0 \leq j \leq 2m$). The frame mask windows 41 separate the channels formed by the frame mask detectors 25. The frame mask windows 41 have the same widths as the detectors 25 ($2\pi/(4m+2)$). In medical applications, the following examples can be provided: diameter of the unit disk: 60 cm, radial width of each detector (each window): 1 mm, number of detectors/windows: 1000. Axial width of the frame mask: 0.5 to 50 mm for the case of reconstructing 2-dimensional images. With other applications, e.g. in micro CT applications, other sizes can be used.

The second main part of the imaging device is the source-detector-unit 51 with the X-ray source 11 and the outer detector device 21 (see FIG. 1). The source-detector-unit 51 is movable on the carrier around the centre of the unit disk (or another fixed point). The distance between the X-ray source 11 and the outer detector device 21 is more than the diameter of the unit disk, so that both the (near) X-ray source 11 and the (wide) outer detector device 21 of the source-detector-unit 51 are outside the frame mask 40. The outer detector device 21 comprises a detector array, which is partitioned into several detector channels, whose widths depend only on the distance of the detector device 21 and the radius of the unit disk. With a curved detector array, the widths of the detector channels depend on the curvature.

Figure 5:
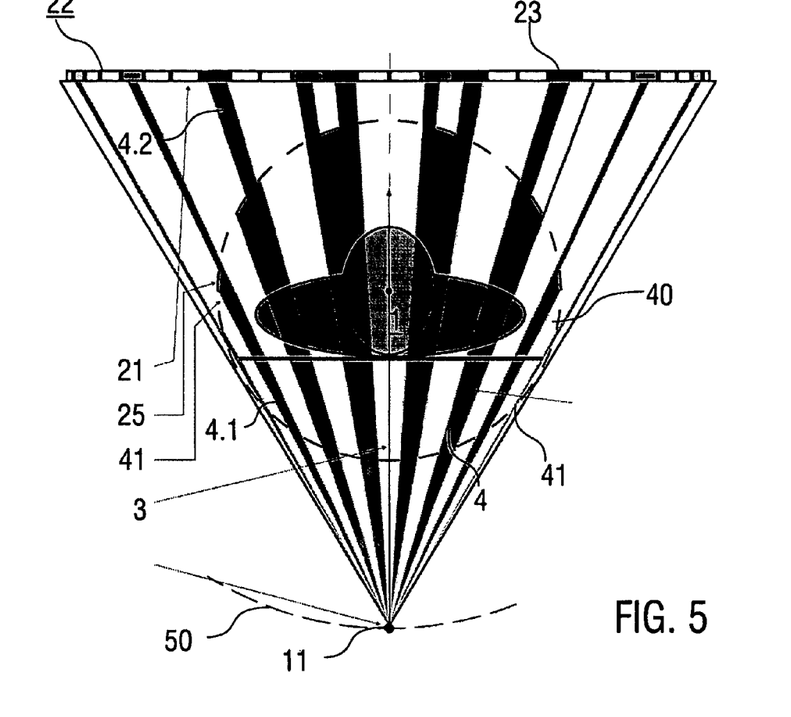

In FIG. 2, the outer detector device 21 is shown as an arc, but it could also be a flat panel fitted with detectors as shown in FIG. 5. Generally, the X-ray source 11 is positioned and moved as close to the ROI as possible (FIGS. 1, 2). However, this feature is not strictly necessary. The X-ray source 11 could be arranged with a larger distance (e.g. in medical applications in the range of 15 cm to 100 cm).

The X-rays emitted from the X-ray source 11 are transmitted through the frame mask windows 41 in the near end of the frame mask 40, which serves as a beam shaping device. Accordingly, a fan of several X-ray beam components are formed with thickness specified below.

The X-ray beam components transmitted through the frame mask windows 41 will hit the far side of the unit disk. Some of the beam components will hit the frame mask detectors 25 on the inner surface of the frame mask 40, while other beam components will pass the frame mask windows 41 in the far end of the frame mask 40 and hit the detector array 22 of the outer detector device 21 (wide end of the source-detector-unit 51). A first group of attenuation values measured with the outer detector device 21 are called dynamic data, while a second group of attenuation values measured with the fixed frame mask detectors 25 are called stationary data.

2. Imaging Method of the Invention

Figure 3:
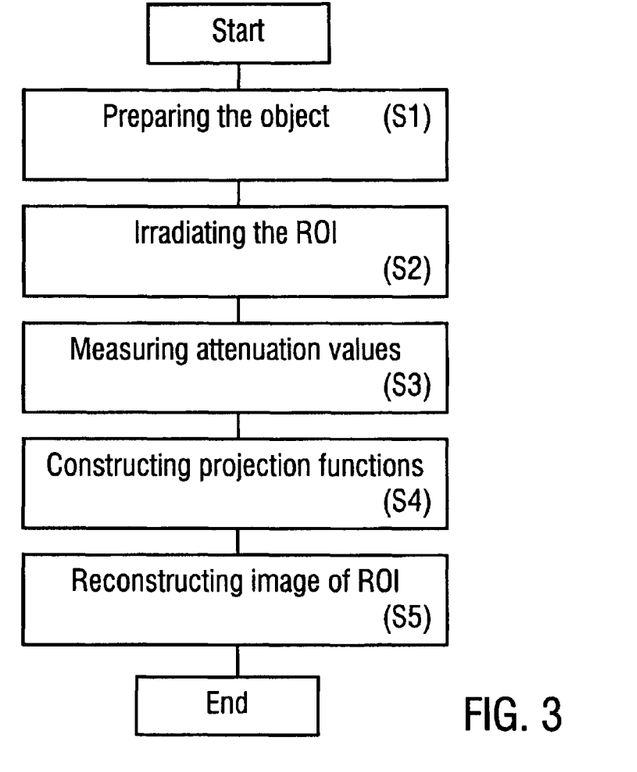
FIG. 3 a flow chart illustrating an embodiment of the imaging method according to the invention.

In FIG. 3, the steps for carrying out the imaging method of the invention are summarized. Firstly, the object to be investigated, like e.g. the head or another part of a patient's body is prepared (step S1). Preparing the object comprises a positioning of the object on the holding device 30 in a CT gantry such that the region of investigation is aligned with the source-detector-unit 51 and the frame mask 40 (see FIG. 1). Subsequently, the object is subjected to the irradiation (step S2). The X-ray source 11 is operated for generating a fan or cone X-ray beam directed towards the object and the detector device 20. The X-ray beam is transmitted through the frame mask 40 such that X-ray beam components are formed by the frame mask windows 41. Measuring integrated attenuation values (step S3) comprises sensing X-rays received with the outer detector device 21 and with the frame mask detectors 25. The steps S2 and S3 are continuously conducted for measuring at a plurality of projection directions of irradiating the X-rays through the object 1. The projection directions are set with a complete rotation of the source-detector-unit 51 on the carrier 50. Step S3 automatically includes a discretization of data. Due to the detection geometry of the invention, discrete attenuation value data are recorded. The attenuation values measured with the outer detector device 21 and the frame mask detectors 25 form the first and second groups of integrated attenuation values, which are subjected to the steps of constructing the projection functions (step S4) and data processing for reconstructing an image of the ROI (step S5).

During at least one of steps S1 to S3, the object can be further manipulated, e.g. by adding a contrast agent or by an intervention. This embodiment of the invention has particular advantages for collection of dynamic images or imaging changing objects in particular in medical applications of the imaging method.

The step of constructing the projection functions (step S4) is described with further details below. Each projection function comprises a plurality of parallel projections, which are obtained by an assignment of the beam components measured with the detector device 20. With the assignment, the fan beam geometry becomes a parallel geometry as required for reconstructing an image from the Radon data.

Figure 4:
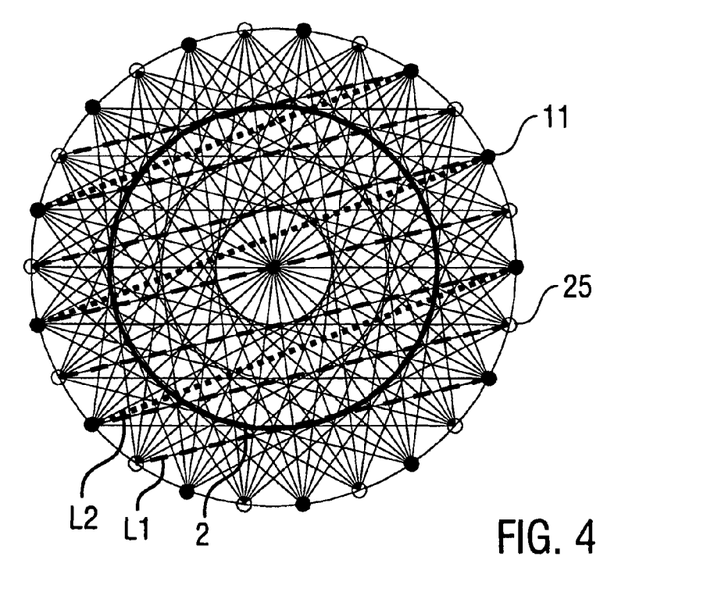
FIGS. 4 to 12 diagrams illustrating the principles of Radon data collection according to the invention.

In FIG. 4, the assignment of the fan of X-ray beam components to groups of parallel X-ray beam components is schematically illustrated. The solid bullets on the circumference of the outside circle in FIG. 4 denote the centre positions of the frame mask windows through which beam components from the X-ray source 11 are transmitted, while the small circles denote the frame mask detectors 25. Only those lines having an intersection with the ROI 2 (the inner disk) are depicted. The X-ray beam components that emit from the X-ray source 11 to the frame mask detectors 25 automatically become parallel lines. As an example, the dashed lines L1 represent a first set of parallel beams. On the other hand, the X-ray beam components that emit from the X-ray source 11 to the outer detectors 23 become parallel lines as well. The directions of these projections are those of lines from sources 11 through frame mask windows between the frame mask detectors 25. As an example, the dotted lines L2 represent a second set of parallel beams.

For a set of parallel lines obtained from assignment as described in FIG. 4, the parallel dashed lines are located on the Chebyshev points $\cos(2j+1)\pi/(2m+1)$, $j=0, 1, \ldots 2m$, on the axis that is perpendicular to the parallel direction and has a centre at the origin of the unit disk. EP 04031043.5 is introduced into the present specification in particular with regard to the description of further details of the Chebyshev points.

3. Collection of Dynamic Data

The collection of the dynamic data is described with reference to FIGS. 5 to 8. FIG. 5 illustrates the object 1 on the holding device 30 surrounded by the frame mask 40. The X-ray source 11 is arranged on the carrier 50. The outer detector device 21 with a straight line-shaped detector array 22 is arranged on the carrier 50 opposite to the X-ray source 11. The detector array 22 comprises a plurality of sensor elements 23. Each sensor element 23, which consists of a single sensor or a sub-array of connected single sensors, is arranged for detecting one energy beam component passed through a respective pair of frame mask windows. Accordingly, each sensor element 23 represents one detection channel of the outer detector device 21. As the projections through pairs of frame mask windows have a decreasing width with increasing fan angle, the sizes of sensor elements 23 are decreasing from the centre to both ends of the detector array 22.

The frame mask 40 includes N frame mask windows 41. In the present description, the number N of frame mask windows 41 is assumed to be odd. The implementation of the invention is not restricted to this embodiment. The case with even N can be considered in an analogous way.

The fan beam 3 emitted from the X-ray source 11 is converted into a plurality of X-ray beam components 4. Depending on the relative position of the X-ray source 11 and the frame mask windows 41, the complete X-ray beam components or parts thereof (4.1, 4.2) hit the frame mask detectors (e.g. 25) on the inner surface of the frame mask 40 or the sensor elements (e.g. 23) of the outer detector array 22 respectively. Reordering or assigning the energy beam components transmitted to the outer detector device 21 leads to the dynamical data, which are represented as parallel X-ray beam components 5 in FIG. 6.

Figure 6:
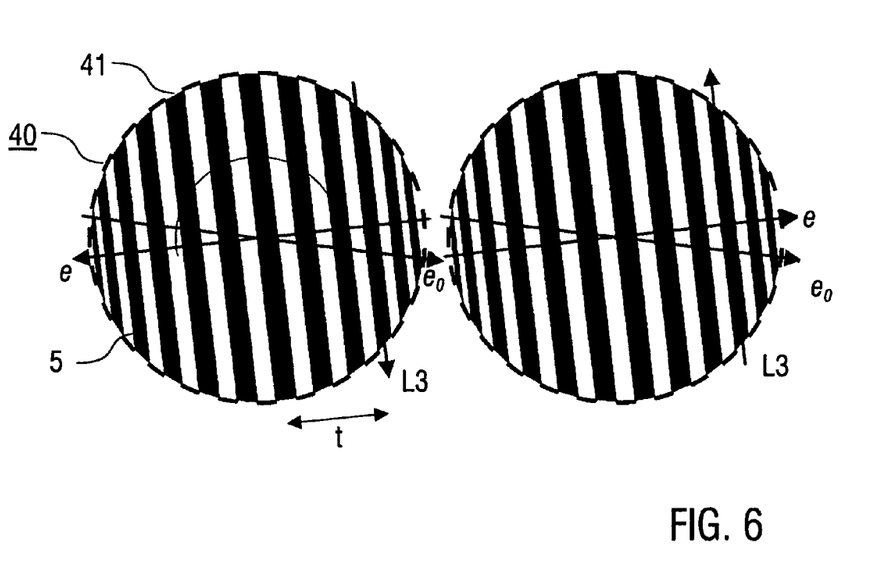

In FIG. 6, the stationary frame mask 40 (radius r) is depicted together with the parallel set of X-ray beam components 5. Each of the black stripes corresponds to a detector channel of the outer detector device. The geometry of these stripes is defined by "window-to-window" pairs and may be described by two parameters t and φ. The parameter t is the signed distance between the centre of the stationary frame mask 40 and the line connecting the centres of the corresponding frame mask windows 41 (e.g. line L3 in FIG. 6). The parameter φ is the angle between the initial direction $e_0$ and the direction, which is perpendicular to L3 (direction e in FIG. 6).

The stripes are represented with the following dual representation:

$$\varphi_j^0 = \delta + \frac{2\pi j}{N}, j = 0, \ldots, N-1, \quad (1)$$

$$\theta_i^0 = \frac{(1+2i)\pi}{N}, t_i^0 = r\cos\theta_i^0, i = 0, \ldots, (N-3)/2;$$

$$\varphi_j^1 = \delta + \frac{(1+2j)\pi}{N}, j = 0, \ldots, N-1, \quad (2)$$

$$\theta_i^1 = \frac{2\pi i}{N}, t_i^1 = r\cos\theta_i^1, i = 1, \ldots, (N-1)/2,$$

Wherein $\delta$ is the angle, which determines $e_0$ in a fixed coordinate system.

One of the representations (1) and (2) is redundant. The following relations of equivalence are valid:

$$(\phi_j^0, t_i^0) \Leftrightarrow (\phi_{j+(N-1)/2}^1, t_{i+(N-1)/2}^1), 0 \leq j \leq (N-1)/2, 0 \leq i \leq (N-3)/2 \quad (3)$$

$$(\phi_j^1, t_i^1) \Leftrightarrow (\phi_{j-(N+1)/2}^0, t_{i-(N-1)/2}^0), 0 \leq j \leq (N-3)/2, 1 \leq i \leq (N-1)/2 \quad (4)$$

The number of pairs describing the stripes given by (2) (reference numeral 5 in FIG. 6) is exactly two times bigger than the number of all stripes (X-ray beam components) as each stripe is passed twice during one cycle of rotation of the X-ray source around the fixed frame mask 40.

The outer detector device 21 receives only those photons whose path lie entirely in one of the described stripes. Accordingly, between the sensor elements 23 of the outer detector device 21 and the stripes there exists the following correspondence. Counting the sensor elements counter clockwise with zero offset, the k-th sensor element is related to the stripe $(\phi_i^b, t_i^b)$, j=0, ..., N-1 where b=k mod 2 and l=(k+b)/2. Conversely, the photons with paths lying in the stripes $(\phi_i^b, t_i^b)$, j=0, ..., N-1, are received in the sensor element 2 l-b. As the result of this correspondence, there is a one-to-one map between the sensor elements of the outer detector device and the parameters $t_i^b$. Therefore, each sensor element can be simply identified and read on the basis of the corresponding parameter $t_i^b$. From the above relations of equivalence (3) and (4) it follows that the sensor elements $t_i^0$ and $t_{(N-1)/2-i}^0, 0 \leq i \leq (N-3)/2$ (or: $t_i^1$ and $t_{(N-1)/2-i}^1, 0 \leq i \leq (N-3)/2$) collect the information on the same stripes. This phenomenon can be explained by a dual character of positions of the X-ray source relative to the corresponding X-ray beam component. The corresponding sensor elements are called "equivalent". Two sets of parallel X-ray beam components detected with equivalent sensor elements are depicted in FIG. 6.

During the rotation of the source-detector-unit 51, a single sensor element of the outer detector device receives information from a large set of X-ray beam components. The way this information is treated is described below with reference to FIG. 7.

Figure 7:
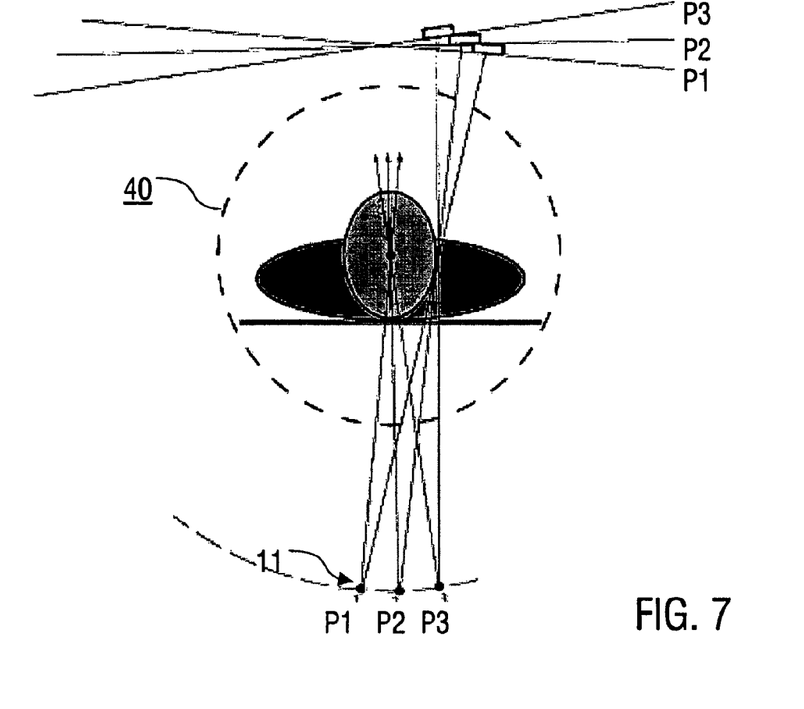

In FIG. 7, three control positions of a single sensor element 23 are depicted. The sensor element 23 receives photons between the positions P1 and P2 of the X-ray source 11, while it is screened by the frame mask 40 between the positions P2 and P3. Accordingly, the position P1 can be interpreted as a "switch-on", position P2 as "switch-off" and position P3 as "switch-on" again. In the time interval between "switch-on" and "switch-off", information about only one distinct X-ray energy beam component (stripe) is collected. The "switch-on"-points $\beta_i^b(j)$ of a single sensor element $t_i^b$ are uniformly distributed on the circular trajectory of the X-ray source with an angle increment $2\pi/N$ and can be described as follows:

$$\beta_i^b(j) = \varphi_i^b - \frac{\pi}{2N} - \left(\frac{\pi}{2} - \arcsin\frac{t_i^b}{R}\right) \quad (5)$$

where R is a radius of the source trajectory. The set of corresponding "switch-off"-points is simply shifted relative to the "switch-on" set by the angle $\pi/N$.

On the basis of equation (5), the dynamic data can be read out from the sensor elements and assigned to a predetermined order of parallel channels which provides the input for the image reconstructing step S5 (FIG. 2).

Figure 8:
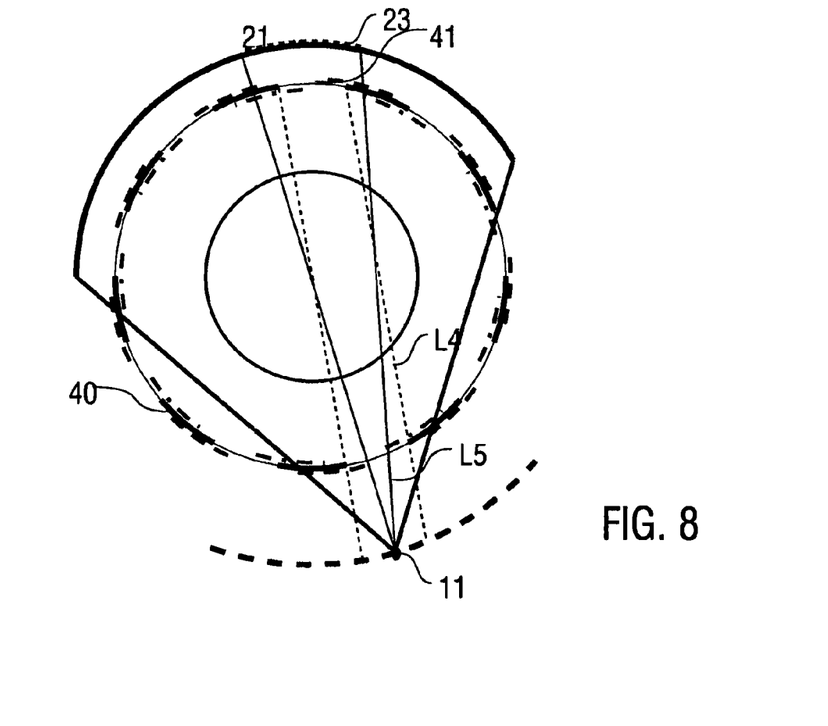

A modified description of the dynamic data collection is shown in FIG. 8. This description corresponds to a modified embodiment of the invention. It is based on the feature that the source-detector-unit 51 is fixed but the disk with the frame mask rotates. In FIG. 8, the solid arcs represent one position of the frame mask 40, and the two dashed lines L4 are drawn to mark the particular frame mask window 41 through which X-rays are transmitted to the outer detector device 21. The outer detector device 21 is depicted as comprising a plurality of sensor elements 23. The dashed and dash-dotted arcs indicate two more positions of the frame mask 40 relative to the source-detector-unit 51, which are two extreme positions that define the sizes of the channel on the detector as indicated by the two solid lines L5. The solid line on the left marks the position when the X-ray source 11 is lined up with the two end points of the frame mask windows 41 and when the frame mask 40 is in the position marked by the dashed arc, and the solid line on the right marks the same line-up when the frame mask is in the position marked by the dash-dotted arc.

As the frame mask 40 and the source-detector-unit rotate relative to each other (in practice: when the source-detector-unit rotates), the X-rays emitted from the X-ray source 11 through these two particular frame mask windows are collected by the channel of the outer detector device 21. Accordingly, the channels of the detector device are defined. The accumulation of the photons detected represents the data for the X-ray beam component from the frame mask window at the bottom to the frame mask window at the top. These data are also assigned to parallel rays, whose directions are those of dotted lines L2 shown in FIG. 4.

The resulting dynamic data are represented as $$R_2 := \left\{ R_{2\nu+1}\left(\frac{2j\pi}{2m+1}\right) : 0 \leq \nu \leq 2m, 1 \leq j \leq m \right\}. \quad (6)$$

4. Collection of Stationary Data

Figure 9:
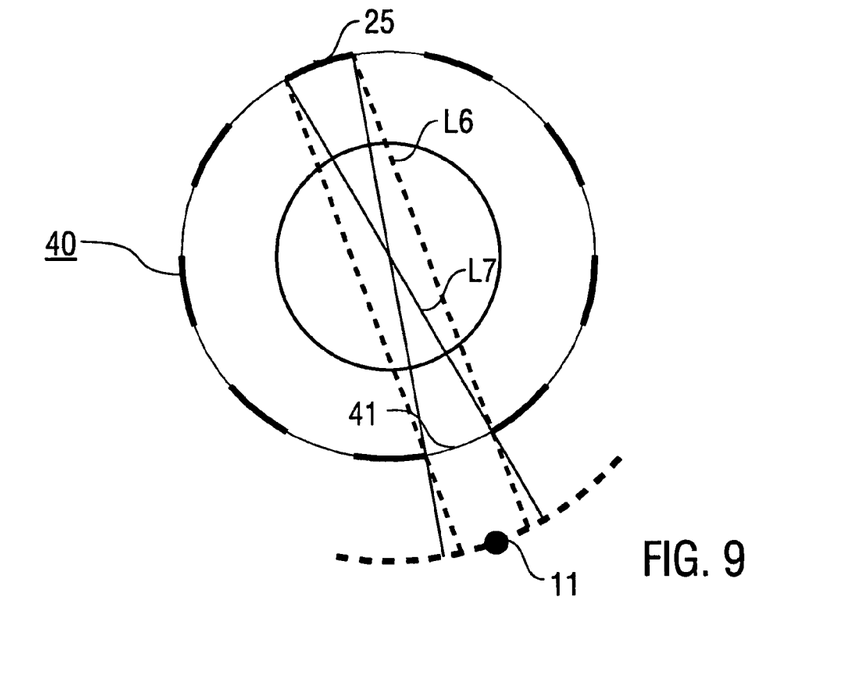

In FIG. 9, the collection of the stationary data by measuring the second group of integrated attenuation values is illustrated. One channel of the frame mask detectors 25 is marked and the X-ray beam component through one of the frame mask windows 41 is indicated. The two dashed lines L6 indicate the X-ray beam component that is transmitted via the frame mask window 41 to the frame mask detector 25, while the solid lines L7 indicate the extreme positions of the X-ray source 11 as it moves around the unit disk. When the source is inside the arc between the solid lines L7, the X-ray beam component it emits will hit the frame mask detector 25. The accumulation of photons detected represents the integrated attenuation values for the X-ray beam component from the frame mask window 41 to the frame mask detector 25.

Figure 10:
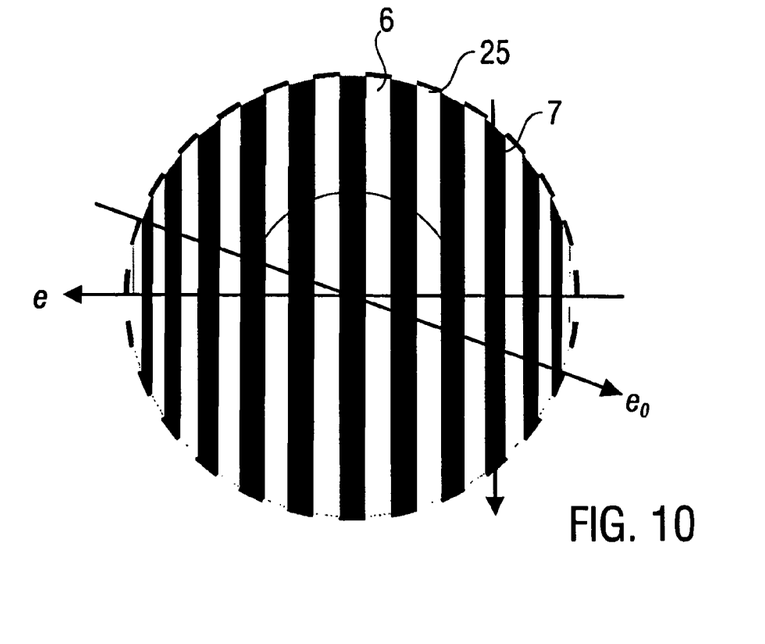

After the step of assignment, the configuration of a parallel set of X-ray beam components received by the frame mask detectors 25 can be represented as shown in FIG. 10. Contrary to the representation of FIG. 6, the stationary data are represented on the basis of "window-to-detector"-pairs. Grey (6) and black (7) stripes represent two sets of parallel X-ray beam components. Each of the stripes can be uniquely described by a pair ($\phi_j$, $t_i$), where $$\varphi_j = \delta + \frac{2\pi}{N} j, \ j = 0, \ldots, N-1, \tag{7}$$

$$t_i = r\cos\theta_i, \ \theta_i = \frac{(1+2i)\pi}{2N}, \ i = 0, \ldots, N-1$$

Each sensor element of the frame mask detector 25 can be simply identified with $\phi_j$, j=0, ..., N−1 via the relation $$\tilde{\theta} j = \varphi_k - \frac{1}{2}\frac{\pi}{N} \tag{8}$$

where $\tilde{\theta}j$ are the angle coordinates of the sensor element centres.

Figure 11:
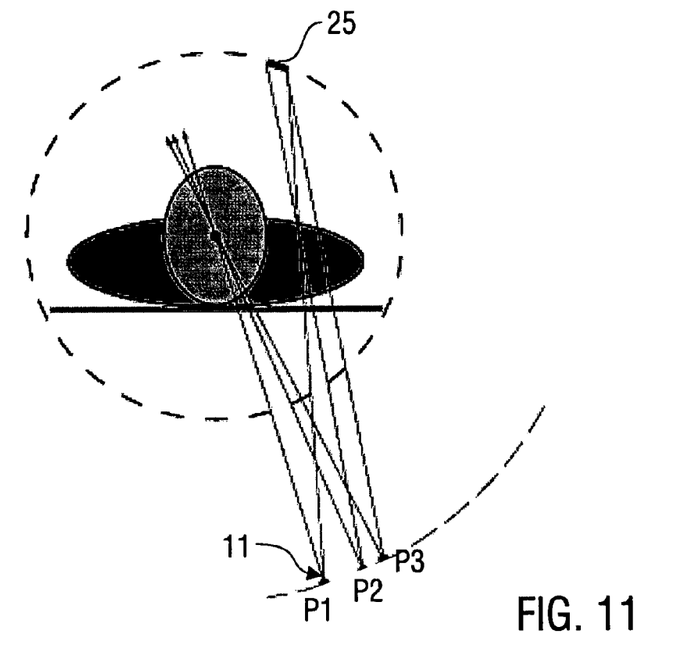

FIG. 11 illustrates that the activity of a single sensor element of the frame mask detector 25 occurs in an "switch-on"-"switch-off" regime, as in the case of the collection of dynamic data. With a counterclockwise rotation of a source-detector-unit 51, activity of frame mask detector 25 is switched on in position P1 of the X-ray source 11, while it is switched-off in position P2 and switched-on in position P3 again.

Figure 12:
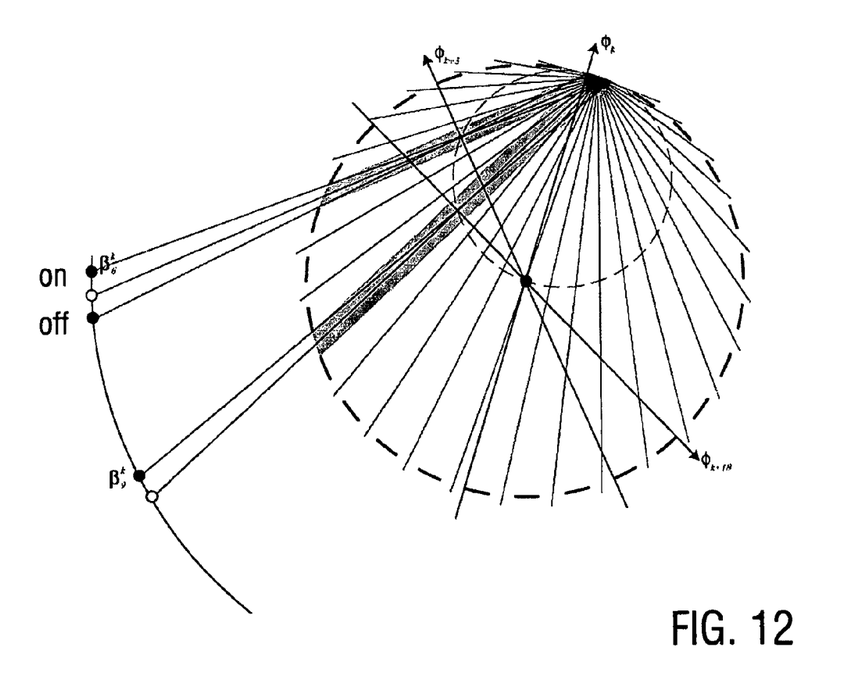

During the rotation around the stationary frame mask 40, the X-ray source emission hits a particular frame mask detector 25 in an alternative off-on order as shown in FIG. 12. Each distinct hit corresponds to a certain X-ray beam channel converging to the frame mask detector 25 from the frame mask window 41 traversed by the X-ray source 11. With a counterclockwise rotation of the X-ray source 11, the set $\Omega_k$ of stripes that converge to the detector element 25 ($\phi_k$) can be described as follows.

$$m_{2j}^k = (k+j) \bmod N, \ j = 0, \ldots, (N-1)/2, \tag{9}$$

$$m_{2j+1}^k = (k + (N+1)/2 + j) \bmod N, \ j = 0, \ldots, (N-3)/2,$$

and $$n_j = \begin{cases} j, & \text{for } j \text{ even,} \\ N-1-j, & \text{for } j \text{ odd.} \end{cases}$$

Then $$\Omega_k = \left\{ \left(\varphi_{m_j^k}, t_{nj}\right) \right\} j = 0, N-1$$

The coordinates ($\beta^j_k$) of the "switch-on"-positions for the detector element ($\phi_k$) are:

$$\beta^j_k = \varphi_{m_k^j}, -\frac{\pi}{2N} + s\left(\frac{\pi}{2} - \arcsin\frac{t_{nj}}{R}\right) \tag{10}$$

where s=1 if j is even and −1 otherwise. The coordinates of "switch-off" positions for the frame mask detectors are $\beta^j_k$+ π/N.

The appropriate recording of the output signals of sensor elements is based on the above on-off switching regime of the sensor elements activity together with the information of the corresponding control points defined in equations (5) and (10). The recording step can be implemented with different ways. Firstly, each distinct sensor element can be associated with an N-dimensional matrix. Each hit impulse for a given sensor element is recorded into a corresponding cell of its matrix. The recording into the matrix is complete after one cycle of rotation of the source-detector-unit 51 around the stationary frame mask.

The hit pulse has a finite length, i.e. defined on the finite interval or the impulse support. The values of the signal in the points of the impulse support are related to the numbers of photons instantly detected by the sensor elements. The integral over the impulse support provides the whole number of photons detected by the sensor element while the traversing over the single X-ray beam channel.

For a 2-dimensional image described by a function $f(x, y)$ defined on the unit disk $B^2 = \{(x,y):x^2+y^2 \leq 1\}$, a Radon projection is a line integral as follows:

$$R_\theta(f;t) := \int_{I(\theta,t)} f(x,y) dx dy, \ 0 \leq \theta \leq 2\pi, \ -1 \leq t \leq 1, \tag{11}$$

where $I(\theta,t) = \{(x,y): x\cos\theta + y\sin\theta = t\} \cap B^2$ is a line segment inside $B^2$. A thick ray means an average (integral of the Radon projections). In the present specification, the same notation is used for Radon data, whether the X-ray beam component is thick or not. Accordingly, the Radon data are indicated with:

$$R_\nu(\theta) := R_{\xi_\nu}(f; \cos\theta), \tag{12}$$

$$\xi_\nu = \frac{\nu\pi}{4m+2}, \ 0 \leq \nu \leq 4m.$$

The attenuation values collected in the plurality of frame mask detectors can be assigned to parallel rays for the OPED algorithm following the geometry illustrated in FIG. 4. There are 2m+1 views and M=2m+1 X-ray beam components per view that intersect the ROI, whose Radon data are registered by the frame mask detectors 25. The set of data is represented by:

$$R_1 := \left\{ R_{2\nu}\left(\frac{2j+1}{4m+2}\right) : 0 \leq \nu \leq 2m, \ 0 \leq j \leq 2m \right\} \tag{13}$$

wherein the data, whose X-ray beam components are outside the ROI should be taken as zero.

5. Application of the OPED Algorithm

As the source-detector-unit 51 moves along the disk, the Radon data comprising stationary and dynamic data are collected. Together, the stationary data and the dynamic data are used to reconstruct the image of ROI (step S5 in FIG. 2). The algorithm used for reconstruction preferably is based on the OPED algorithm in two different types of geometries as described below. The description of the image construction algorithm described in EP 04031043.5 is introduced into the present specification by reference. In the following, the modification of the OPED algorithm for reconstructing an image on the basis of the stationary and dynamic data is described.

Every square integrable function on the unit disk B can be represented as a sum $$f(x, y) = \sum_{k=0}^{\infty} proj_k f(x, y), \tag{14}$$

where $proj_n f$ is the projection of $f$ on the subspace of orthogonal polynomials of degree n. The equality means that $$\lim_{n \to \infty} S_n f(x, y) = f(x, y), \quad (15)$$

where $$S_n f(x, y) = \sum_{k=0}^{n} \text{proj}_k(x, y)$$

in $L^2(B)$ norm. The function $S_n f$ is the n-th partial sum of the orthogonal expansion and it is the best polynomial approximation of $f$ in $L^2$ norm.

The modified algorithm is based on the following formula for $S_n f(x,y)$:

$$S_n(f; x, y) = \sum_{v=0}^{2n+1} \frac{1}{\pi} \int_{-1}^{1} R_{\xi_v}(f; t) \Phi_v(t; x, y) dt \quad (16)$$

where $$\Phi_v(t; x, y) = \frac{1}{2n+2} \sum_{k=0}^{n} (k+1) U_k(t) U_k \begin{pmatrix} x \cos \frac{v\pi}{2m+1} + \\ y \sin \frac{v\pi}{2m+1} \end{pmatrix}. \quad (17)$$

For deriving the modified OPED algorithm from equation (16), two different quadrature formulas are used for the integrals in $S_{2m}$ (n=2m).

$$\frac{1}{\pi} \int_{-1}^{1} f(t) \frac{dt}{\sqrt{1-t^2}} \approx \frac{1}{2m+1} \sum_{j=0}^{2m} f\left(\cos \frac{(2j+1)\pi}{4m+2}\right), \quad (18)$$

$$\frac{1}{\pi} \int_{-1}^{1} g(t) \sqrt{1-t^2} \, dt \approx \frac{1}{2m+1} \sum_{j=1}^{2m} \sin^2 \frac{j\pi}{2m+1} g\left(\cos \frac{j\pi}{2m+1}\right). \quad (19)$$

With the imaging method of the invention, two groups of data are collected. Additionally to the dynamical data $R_2$ according to equation (6), the stationary data $$R_{2v+1}\left(\frac{(2j+1)\pi}{2m+1}\right)$$

are considered, whose directions are lines from the small circles to small circles in FIG. 4. To this end, an interpolation between the measured values of subsequent frame mask detectors is used.

For the stationary data $R_1$ in equation (13), equation (18) is used. This leads to the sum $$A_{2m}^{(1)} f(x, y) = \sum_{v=0}^{2m} \sum_{j=0}^{2m} R_{2v}\left(\frac{(2j+1)\pi}{4m+2}\right) T_{j,v}^{(1)}(x, y), \quad (20)$$

where $$T_{j,v}^{(1)}(x, y) = \frac{1}{2m+1} \sin \frac{(2j+1)\pi}{4m+2} \Phi_v(\cos \xi_{2j+1}; x, y). \quad (21)$$

For the dynamical data $R_2$ in equation (6), equation (19) is used. This leads to the sum $$A_{2m}^{(2)} f(x, y) = \sum_{v=0}^{2m} \sum_{j=1}^{2m} R_{2v+1}\left(\frac{j\pi}{2m+1}\right) T_{j,v}^{(2)}(x, y), \quad (22)$$

where $$T_{j,v}^{(2)}(x, y) = \frac{1}{(2m+1)} \sin \frac{j\pi}{2m+1} \Phi_v(\xi_{2j}; x, y). \quad (23)$$

The final reconstruction step is given by the average of the above two terms:

$$A_{2m} f(x, y) = \frac{1}{2} [A_{2m}^{(1)} f(x, y) + A_{2m}^{(2)} f(x, y)]. \quad (24)$$

The mathematical description below refers to a disk surrounded by a circle. It is emphasized that an analogue consideration can be done for a region surrounded by an ellipse. With the equation of the ellipse $(x^2/a^2)+(y^2/b^2)=1$, a change of variables x=au and y=bv leads back to the case of the disk $u^2+v^2=1$. Further modified shapes are possible if corresponding changes of variables can be introduced. The building of corresponding frame masks is possible, but not as suitable as a circle or an ellipsoid mask cross-section in view of the algorithm.

For further details of mathematical tools used herein, reference is made to the publications of R. Marr: "On the reconstruction of a function on a circular domain from a sampling of its line integrals" in "J. Math. Anal. Appl."[1] vol. 45, 1974, p. 357-374; F. Natterer: "The mathematics of computerized tomography" Reprint of the 1986 original "Classics in Applied Mathematics 32" SIAM, Philadelphia, Pa., 2001; F. Natterer and F. Wuebbeling by "Mathematical Methods in Image Reconstruction" SIAM, Philadelphia, Pa., 2001; C. Dunkl and Yuan Xu: "Orthogonal polynomials of several variables", Cambridge University Press, 2001; Yuan Xu "Funk-Hecke formula for orthogonal polynomials on spheres and on balls" in "Bull. London Math. Soc." vol. 32, 2000, p. 447-457; and Yuan Xu "Representation of reproducing kernels and the Lebesgue constants on the ball" in "J. Approximation Theory" vol. 112, 2001, p. 295-310.

6. Application of Other Algorithms

According to another embodiment of the invention, step S5 (FIG. 3) may comprise an application of the FBP algorithm. The FBP algorithm can be applied on the collected first and second groups of data separately with a subsequent superposition of the resulting partial image. Alternatively, the FBP algorithm can be applied on all collected data simultaneously.

7. Recording of 3-Dimensional Images

With the detection geometry of the invention, helical projection data can be processed for obtaining 3-dimensional images of the object. Accordingly, at least one of the object and the source-detector unit is translated in a predetermined direction, e.g. perpendicular to the projection directions during the step S2 of irradiating the object for obtaining the helical projection data. Preferably, the object under investigation, e.g. a patient, is shifted through the CT gantry, lying on a patient table, which is moving continuously.

For collecting the helical projection data, the planar ring-shaped frame mask can be used, which is described above. In this case, the frame mask is movable relative to the object e.g. perpendicular to the plane including the projections directions. Alternatively, the frame mask has a tube-shape extending over the whole length of the object to be imaged. The tube-shaped frame mask has frame mask windows extending as spiral or straight windows along the longitudinal direction of the tube. Furthermore, the tube-shaped frame mask can be used in combination with a fixed tube-shaped outer detector and/or a fixed multi-focus source device.

By this method a so-called helical or spiral CT data set can be gathered, including both first and second groups of attenuation values. In particular, the helical CT data set can be reconstructed in an analogue way as described above for obtaining a stack of 2-dimensional images which are combined to a 3-dimensional image of the object.

The invention claimed is:

1. An imaging method for imaging a region of investigation of an object, comprising the steps of:
    generating an energy input beam with an energy beam source;
    irradiating the region of investigation with energy input beam components of the energy input beam along a plurality of projection directions, the energy input beam components being formed with a frame mask being arranged between the energy input beam and the object and including frame mask window;
    measuring first integrated attenuation values of the energy input beam components with an outer detector device arranged outside the frame mask;
    measuring second integrated attenuation values of the energy input beam components with a frame mask detector device being arranged on an inner surface of the frame mask; and
    reconstructing an image of the region of investigation based on the first and second integrated attenuation values.

2. The method of claim 1, wherein the step of reconstructing the image comprises determining an image function as a superposition of a first sum of polynomials multiplied with values of first projection functions obtained from the first integrated attenuation values and a second sum of polynomials multiplied with values of second projection functions obtained from the second integrated attenuation values.

3. The method of claim 2, wherein the first and second projection functions are obtained from the first and second integrated attenuation values measured for first and second groups of parallel energy input beam components, respectively.

4. The method of claim 1, wherein the step of reconstructing the image comprises the step of determining an image function by a filtered back projection algorithm.

5. The method of claim 1, wherein the irradiating step comprises setting the projection directions by moving the energy beam source and the frame mask relative to each other.

6. The method of claim 1, wherein the irradiating step comprises measuring the second integrated attenuation values according to the projection directions while moving the outer detector device and the frame mask relative to each other.

7. The method of claim 5, wherein the frame mask and the object have a fixed position and at least one of the energy beam source and the outer detector device are moved around the frame mask.

8. The method of claim 7, wherein the energy beam source and the outer detector device are simultaneously moved around the frame mask.

9. The method of claim 8, wherein the energy beam source and the outer detector device are rotated on a carrier around the frame mask.

10. The method of claim 5, wherein the energy beam source and the outer detector device have a fixed position and the frame mask and the object are moved relative to the energy beam source and the outer detector device.

11. The method of claim 10, wherein the frame mask and the object are rotated relative to the energy beam source and the outer detector device.

12. The method of claim 1, wherein the energy beam source, the outer detector device, the frame mask and the object are fixed relative to each other and the irradiating step comprises the step of setting the projection directions by operating a multi-focus source.

13. The method of claim 1, wherein the energy beam source comprises an X-ray source.

14. The method of claim 1, comprising the step of reconstructing a 3-dimensional image of the object by imaging a plurality of regions of investigation.

15. An imaging device for imaging a region of investigation of an object, comprising:
    an energy beam source device being adapted for irradiating the object;
    a detector device being adapted for measuring radiation from the energy beam source device transmitted through the object;
    a holding device for holding the object; and
    a frame mask surrounding the holding device and comprising frame mask windows, wherein
    the energy beam source device is arranged on an outer side of the frame mask, and
    the detector device comprises an outer detector device arranged on the outer side of the frame mask and a frame mask detector device arranged on an inner surface of the frame mask.

16. The imaging device of claim 15, wherein the frame mask comprises a ring mask.

17. The imaging device of claim 15, wherein the frame mask is fixed relative to the holding device.

18. The imaging device of claim 15, wherein at least one of the energy beam source device and the outer detector device is movably arranged on a carrier.

19. The imaging device of claim 18, wherein the energy beam source device and the outer detector device are adapted to be rotated on the carrier around the frame mask.

20. The imaging device of claim 19, wherein the energy beam source device and the outer detector device are arranged in a computer tomography gantry.

21. The imaging device of claim 15, wherein the frame mask and the holding device are movable relative to the energy beam source device and the outer detector device, which have a fixed position.

22. The imaging device of claim 15, wherein the frame mask windows have an equal size.

23. The imaging device of claim 15, wherein the frame mask detector device comprises a plurality of frame mask detectors, which are separated from each other by the frame mask windows.

24. The imaging device of claim 15, wherein the frame mask detector device is protected against irradiation by a shielding on an outer surface of the frame mask.

25. The imaging device of claim 15, wherein the energy beam source device comprises an X-ray source.

26. The imaging device of claim 15, further comprising a reconstruction device adapted for reconstructing an image of the region of investigation based on first and second integrated attenuation values measured with the detector device.

* * * * *